US006780630B1

(12) United States Patent
Estes et al.

(10) Patent No.: US 6,780,630 B1
(45) Date of Patent: Aug. 24, 2004

(54) PARENTERAL IMMUNIZATION AGAINST ROTAVIRUS

(75) Inventors: Mary K. Estes, Friendswood, TX (US); Margaret E. Conner, Houston, TX (US)

(73) Assignee: Baylor College of Medicine, Houston, TX (US)

(*) Notice: Subject to any disclaimer, the term of this patent is extended or adjusted under 35 U.S.C. 154(b) by 1826 days.

(21) Appl. No.: 07/911,593

(22) Filed: Jul. 10, 1992

(51) Int. Cl.[7] .............................................. C12N 7/00
(52) U.S. Cl. ...................... 435/235.1; 435/5; 435/236
(58) Field of Search .................... 435/235.1, 5, 236, 435/237; 424/88, 89, 86, 215.1

(56) References Cited

U.S. PATENT DOCUMENTS

| | | | | |
|---|---|---|---|---|
| 4,341,763 A | * | 7/1982 | Zygraich | 424/89 |
| 4,344,935 A | * | 8/1982 | Leclerc et al. | 424/89 |
| 4,636,385 A | * | 1/1987 | Plotkin et al. | 424/89 |
| 4,704,275 A | * | 11/1987 | Wyatt et al. | 424/89 |
| 4,861,864 A | * | 8/1989 | Atkinson et al. | 530/324 |
| 5,147,639 A | * | 9/1992 | Welter et al. | 424/89 |
| 5,474,773 A | * | 12/1995 | Ward | |

FOREIGN PATENT DOCUMENTS

EP                0251467      *    1/1988

OTHER PUBLICATIONS

Flores, J. etal, Comparison of reactogenicity and antigenicity of M37 rotavirus vaccine and rhesus–rotavirus–based quadrivalent vaccine. Lancet 2:33 34, 1990.*
Midthun etal, Reassortant rotaviruses as potential live rotavirus vaccine candidates J. of Virology 53(3):949–954, 1985.*
Clark et al, "Rotavirus Vaccines", in *Vaccines,* Plotkine eds. W. B. Saunders Co. Philadelphia, 1988 pp. 517–525.*
Offit etal J. Infect Dis 152(6):1152–1158, 1985.*
Daum et al, Adv. Pediatr Infect. Dis. 6:1–57, 1991 (pp. 36–38 & 54–56 relevant to rotavirus enclosed).*
Conne et al, "Rotavirus Vaccines & Vaccine Potential" in Current Topics in Microbiology and Immunology 185 Titled *Rotaviruses* Raming ed Springer–Verlag, Berlin, 19: pp. 6 & 285–337.*
Estes et al. Synthesis and Immunogenicity of the Rotavirus . . . J Virol, vol. 61, No. 5, May 1987, pp. 1488–1494.*
Ijaz et al. Effect of different routes of Immunization . . . Antiviral Research, vol. 8, No. 5–6, 1987, pp. 283–298.*
Fields BN et al. "Virology," Lippincott–Raven Publishers, pp. 1657–1708 (1996).*
Tsunemitsu H, et al. "Evidence of serologic diversity within Group C rotaviruses." J. Clin. Microbiol. 30: 3009–3012.*
Kapikian AZ. "A rotavirus vaccine for prevention of severe diarrhoea of infants and young children: Development, utilization and withdrawel." Novartis Found Symp. 238: 153–171 (2001).*

Estes et al, J Gen Virol 43(2): 403–409, 1979.*
Tan et al, Med J Aust, 1(1):19–23, 1981.*
Vaughn et al, Appl Environ Microbiol, 53(9):2218–2221.*
Berman et al, Appl Environ Microbiol 48(2): 317–323, 1984.*
Chen et al, Appl Environ Microbiol 56(5): 1363–1366, 1990.*
Sattar et al, Can J Microbiol 29(10): 1464–1469, 1983.*
Jiang, B. et al. Sequence Analysis of the Gene Encoding VP4 of a Bovine Group C Rotavirus: Molecular Evidence for a New P Genotype; *Virus Genes;* 19:1, 85–88, 1999.
Tsunemitsu, H. et al. Sequence comparison of the VP7 gene encoding the outer capsid glycoprotein among animal and human Group C rotaviruses; *Arch Virol;* 1996; 141(3–4): 705–13.
Mitsutaka, Kuzuya et al.; Molecular Analysis of Outer Capsid Glycoprotein (VP7) Genes from Two Isolates of Human Group C Rotavirus with Different Genome Electropherotypes; *Journal of Clinical Microbiology,* Dec. 1996, pp. 3185–3189.
Coste, Aliz et al.; Nasal Immunization of Mice with Virus–Like Particles Protects Offspring Against Rotavirus Diarrhea; *Journal of Virology,* Oct. 2000, pp. 8966–8971.
Ball, Judith et al; Age–Dependent Diarrhea Induced by a Rotaviral Nonstructural Glycoprotein; *Science;* Apr., 1996; vol. 272, pp. 101–104.
James, Vivienne et al.; Molecular characterization of human group C rotavirus genes 6, 7, and 9; *Journal of General Virology,* 1999, 80 pp. 3181–3187.
Estes, Mary K., *Nucleic Acids Research,* 12:1875–1887 (1984).
Miller, Lois K., *BioEssays,* 11:91–95 (Oct. 1989).
Estes, Mary K., et al., *Immunochemistry of Viruses. The Basis for Serodiagnosis and Vaccines.,* 21:389–405 (1985).
Miller, Lois K., *Genetic Engineering In The Plant Sciences,* 14:203–224 (1981).
Estes, Mary K., et al., *Immunobiology of Proteins and Peptides—III,* 201–2124 (1985).
Kapikian, Albert Z., et al., *Virology,* 37:863–906 (1985).
Mason, Bruce B., *Journal of Virology,* 46:413–423 (1983).
Chan, Wai–Kit, et al., *Virology* 151:243–252 (1986).
Bican, Patrick, et al., *Journal of Virology,* 43:1113–1117 (Sep. 1982).

(List continued on next page.)

*Primary Examiner*—Ali R. Salimi
(74) *Attorney, Agent, or Firm*—Fulbright & Jaworski L.L.P.

(57) ABSTRACT

The invention relates to an improved rotavirus vaccine for man and animals and methods of using them. The invention comprises a method of immunizing humans, particularly children, and animals against rotavirus infections by parenteral immunization. The immunization may be carried out in a series of injections using live or inactivated vaccines, alone or in combination with each other or in combination with a rotavirus subunit vaccine or oral vaccine.

14 Claims, 1 Drawing Sheet

OTHER PUBLICATIONS

Gorziglia, M., et al., *J. Gen. virol.,* 66:1889–1900 (1985).

Beards, G.M., et al., *Journal of Clinical Microbiology,* 19:248–254 (Feb. 1984).

Nakata, Shuji, et al., *The Journal of Infectious Diseases,* 154:448–455 (Sep. 1986).

Estes, Mary K., et al., *Journal of Virology,* 31:810–815 (Sep. 1979).

Smith, Gale E., et al, *Journal of Virology,* 46:584–593 (May 1983).

Both, Gerald W., et al., *Journal of Virology,* 48:335–339 (Nov. 1983).

Estes, Mary K., et al., *Journal of Virology,* 61:1488–1494 (May 1987).

Smith, Gale E., et al. *Proc. Natl. Aad. Sci. USA,* 82: 8404–8408 (Dec. 1985).

Miyamoto, Chikara, et al., *Molecular and Cellular Biology,* 5:2860–2865 (Oct. 1985).

Hambraeus, B. Anna M., et al., *Arch Virol.* 107:237–251 (1989).

Summers, Max D., et al., *Genetically Altered Viruses & The Environment,* Cold Spring Harbor Laboratory 1985, 319–331.

Offit and Dudzik, *J. Clin. Microbiol.* 27:885–888 (1989).

Matsui et al., *J. Clin. Micobiol.* 27:780–782 (1989).

Zissis et al., *J. Infec. Dis.* 148:1061–1068 (1983).

Brussow, Harald, et al., *J. Virol.,* 64:3635–3642 (1990).

Welch, Siao–Kun Wan, et al., *J. Virol.,* 63:000–000 (1989).

Estes, Mary K., et al., "Synthesis and Characterization of Rotavirus Capsid Antigens Using a Baculovirus Expression System," *Abstract U.S.—Japan Cooperative Medical Science Program,* Bethesda, Maryland Oct. 28–30, 1985.

\* cited by examiner

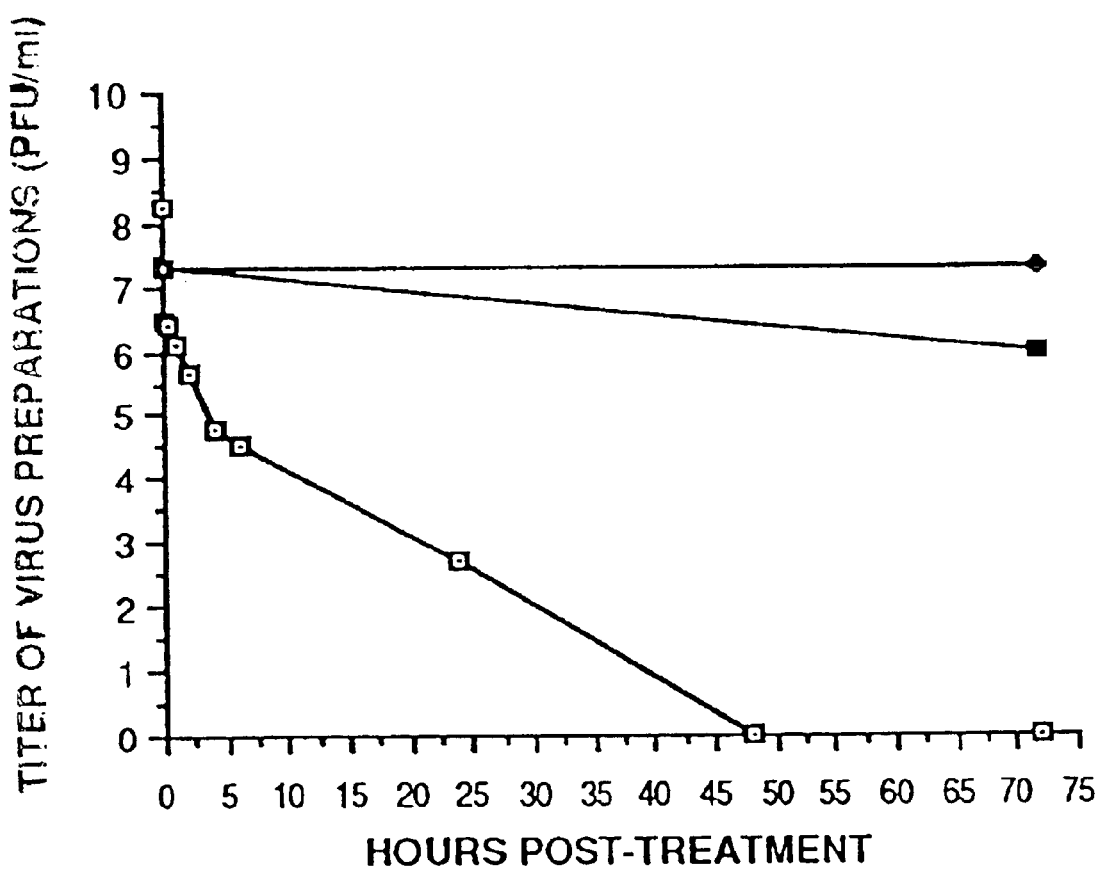

PARENTERAL IMMUNIZATION AGAINST ROTAVIRUS

This invention was supported in part through a grant or award from the National Institute of Health. The U.S. Government, therefore, may have certain rights to this invention.

FIELD OF THE INVENTION

This invention generally relates to the development of vaccines against rotavirus-induced diarrheal disease and methods of using them. More specifically, the invention relates to the development of an improved parenteral immunization using live or inactivated rotavirus preparations, alone or in combination with each other or in combination with an oral vaccine or a rotavirus subunit vaccine.

BACKGROUND OF THE INVENTION

Rotaviruses are the single most important pathogen causing severe diarrhea in children in both developed and developing countries. Conner et al., *Current Topics in Microbiology and Immunology*, in press (1992). Rotavirus infections result in over 500,000 deaths each year among children less than 2 years of age in developing countries. Institute of Medicine, "Prospects for immunizing against rotavirus" in *New Vaccine Development, Establishing Priorities. Vol. 1Diseases of Importance in the United States*. (National Academy Press, Washington D.C. 1985). For children with rotavirus infections in developed countries, the case mortality rate is lower, but hospitalizations are frequent.

In the United States, despite the effectiveness and availability of oral rehydration solutions, about 11% of children with symptomatic rotavirus infections who seek medical care become moderately dehydrated and require hospitalization. Koopman et al., *Am. J. Epidemiol*. 119:114–123 (1984); Rodriguez et al., *Pediatr. Infect, Dis. J.*, 6:170–176 (1987); Glass et al., *J. Pediatr.*, 118:27–33 (1991). The Centers for Disease Control has estimated that 220,000 children are hospitalized for gastroenteritis in the United States each year and that more than half of these children have rotavirus-associated illness. Ho et al., *J. Infect. Dis.*, 158:1112–1116 (1988); LeBaron et al., *Morbid. Mortal. Weekly Rep.*, 39:1–14 (1990); Glass et al. (1991). A recent analysis of the effect of rotavirus infections at a large pediatric hospital in Houston, Tex., estimated that the risk for hospitalization for rotavirus gastroenteritis during childhood is 1 in 48; the extrapolated hospital bed costs alone for the United States were $352 million annually. Matson and Estes, *J. Infect. Dis*. 162:598–604 (1990). This estimate agrees closely with the Centers for Disease Control estimate that the annual inpatient cost of rotavirus-gastroenteritis is one billion dollars. Le Baron et al. (1990). Such data emphasize the need for a vaccine to prevent rotavirus-induced gastroenteritis during the first 2 years of life.

Several strategies have been pursued for development of a rotavirus vaccine for children. Conner et al, (1992); Kapikian et al., Adv. Exp. Med. Biol. 257:67–90 (1990). To date, most effort has been focused on the development and testing of live oral vaccines for children because these were assumed to be necessary to stimulate local mucosal antibody. Kapikian et al. (1990). Unfortunately, vaccination of young children with live oral animal (bovine, rhesus) or human (M37) vaccines or animal-human reassortant vaccines has not yet achieved sufficient take rates with good heterotypic protection in all settings. Conner et al., (1992).

The presence of pre-existing maternal antibody in children administered oral live rotavirus vaccine can interfere with the replication of the vaccine virus, and therefore, reduce the take rate of the vaccine. Cadranel et al.,*J. Pediatr. Gastroenterol. Nutr*. 6: 525–528 (1987); Tajimra et al., *Vaccine* 8:71–74 (1990). Interference by maternal antibody should not be a problem with parenterally administered vaccines. Additionally, multivalent vaccines are being tested to stimulate heterotypic immunity, but achieving a balanced formulation of several live viruses has proven difficult. Perez-Schael et al., *J. Clin. Microbiol*. 28:553–558 (1990); Flores et al., *Lancet* 336:330–334 (1990); Vesikari et al., *Vaccine* 9:334–339 (1991); Wright et al., *J. Infect. Dis*. 164:271–276 (1991).

Alternative strategies using non-replicating subunit vaccines have been proposed, but to date, the ability of such vaccines to induce active protective immunity has not been demonstrated. One reason for this is that relatively few animal models are available to test the ability of a vaccine candidate to induce active protection. For example, only passive protection can be studied in the widely used neonatal mouse model of rotavirus infection because mice are only susceptible to diarrheal disease up to 14 days of age. Wolf et al., *Infect. Immun*. 33:565–574 (1981); Ramig, Microb. Pathog. 4:189–202 (1988).

A model of rotavirus infection in rabbits that mimics infections in children has been developed. The model is useful to monitor the development of active serum and mucosal immunity and protection from challenge against rotavirus. Conner et al., *J. Virol*. 62:1625–1633 (1988); Conner et al.,*J. Virol*. 65:2563–2571 (1991); Thouless et al., *Arch. Virol*. 89:161–170 (1986); Hambraeus et al., *Arch. Virol*. 107:237–251 (1989).

Currently, measurement of protection in the rabbit model is not based on clinical illness, as diarrhea is not consistently seen in the rabbit following rotavirus inoculation due to the extremely efficient fluid absorption of the rabbit cecum. However, histopathologic changes observed over the entire length of the small intestine of infected rabbits (Gilger et al., *Gastroenterology* 194:A146 (1989)), changes in the amount and consistency of intestinal fluid, and the kinetics of virus shedding after infection of antibody-negative rabbits with virulent Ala virus are evidence of productive virus infection, as seen in experimental infections in other animal models and in natural infections in children where clinical diarrhea is observed. Other experiments have shown that detection of infectious virus by plaque assay and excretion of rotavirus antigen by ELISA were of comparable sensitivity. Conner et al. (1988).

The ability of anti-rotavirus IgG to mediate protection has previously been reported in passive protection studies in the suckling mouse model. Offit and Clark, *J. Virol*. 54:58–64 (1985); Offit and Dudzik, *J. Clin. Microbiol*. 27:885–888 (1989); Offit et al., *J. Virol*. 58:700–703 (1986); Matsui et al.,*J. Clin. Micobiol*. 27:780–782 (1989); Sheridan et al.,*J. Infect Dis*. 149:434–438 (1984). The ability of IgG present in the intestine to mediate protection from infection, ameliorate disease, or reduce virus excretion in children has been shown by the use of bovine milk or serum immunoglobulin from hyperimmunized cows for passive treatments in children. Barnes et al., Lancet 1:1371–1373 (1982); Losonsky et al., *J. Clin. Invest*. 76:2362–2367 (1985); Brussow et al.,*J. Clin Microbiol*. 25:932–986 (1987); Hilpert et al., *J. Infect. Dis*. 156:158–166 (1987). Circulating anti-rotavirus antibody which mediated protection in colostrum-deprived calves has been reported following administration of high titer antibody by subcutaneous injection. Besser et al., *J. Virol*. 62:2238–2242 (1988a). This protection was shown to be mediated by the transfer of circulating IgG, to the intestine. Besser et al. (1988a); Besser et al., *J. Virol.* 62:2234–2237 (1988b).

Little information is available on the direct comparisons of live and inactivated virus as it relates to changes in immunogenicity of inactivated rotaviruses. Inactivation of bovine RIT 4237 rotavirus strain by formalin was reported to cause alterations of the virus and parenteral (intramuscular) or intragastric vaccinations with such virus failed to induce cross-protection of piglets challenged with human rotaviruses. Zissis et al., *J. Infec. Dis.* 148:1061–1068 (1983). Inactivation of rotavirus strain RRV by β-propiolactone has been reported to cause changes in VP4 reactivity, determined by comparison of hemagglutination titers of live and inactivated virus, although passive protection of mice pups still was achieved. Offit and Dudzik (1989).

SUMMARY OF THE INVENTION

It is therefore an object of the invention to provide a vaccine against rotavirus that can be used parenterally.

It is a another object of the invention to provide a vaccine against rotavirus that uses live or inactivated rotavirus preparations, alone or in combination with each other and with or without adjuvants.

It is still another object of the invention to provide a live or inactivated vaccine which can be administered alone or in combination with a rotavirus subunit vaccine or oral rotavirus vaccine.

A feature of this invention is that the rotavirus used in the vaccine may be any cultivatable serotype 3 rotavirus or any other cultivatable serotype where a human rotavirus is represented.

Another feature of this invention is that immunization may be achieved by active immunization of the vaccine (infant, adult or animal) or through passive immunization of the infant or young animal by immunization of its mother prior to birth.

One aspect of the present invention is a live or inactivated parenteral vaccine against rotavirus infection comprising a virus classified in a rotavirus serotype which includes at least one human rotavirus.

There is provided in accordance with another aspect of the present invention a method of immunizing humans or animals with a live or inactivated parenteral vaccine against rotavirus infection comprising a virus classified in a rotavirus serotype which includes at least one human rotavirus.

Further objects, features and advantages will be apparent from the following description of the preferred embodiments of the invention.

BRIEF DESCRIPTION OF THE DRAWINGS

FIG. 1. Formalin inactivation curve of SA11 rotavirus. Titers of infectious virus (PFU per milliliter) were determined by plaque assay in MA-104 cells at indicated times for untreated virus (-♦-), virus incubated at 37° C. without addition of formalin (-■-), and virus inactivated with formalin (-□-).

DESCRIPTION OF THE PREFERRED EMBODIMENT

The rabbit has been shown to be a useful model to examine the induction of active immunity and protection against rotavirus. The rabbit model, therefore, was used here to determine whether parenteral vaccination could induce an immune response that protected rabbits from homotypic challenge with a virulent rabbit (Ala) rotavirus. Rabbits were vaccinated with live or inactivated serotype 3 rotavirus, SA11, preparations. The virus may be used by itself as a vaccine. A virus-adjuvant formulation, however, is preferred.

Inactivated virus was prepared by treatment with formalin. Other inactivating agents, e.g., β-propiolactone, or any virus inactivation technique well known in the art also may be used. Inactivation of the virus was determined by plaque assay. Live and inactivated virus preparations were diluted in phosphate-buffered saline (PBS) and combined with one of two adjuvants, either Freund's adjuvant or aluminum phosphate. Freund's adjuvant is a very potent immunomodulating substance. Aluminum phosphate is an FDA-approved adjuvant for use in humans, as is aluminum hydroxide. Other adjuvants such as calcium phosphate, bacille Calmette-Guerin, *Corynebacterium parvum* and *Bordetella pertussis*, are widely used in the art and may be substituted here.

Five to six month old rabbits from a rotavirus free colony were tested. All rabbits, except controls, were vaccinated intramuscularly with virus-adjuvant or PBS- adjuvant formulations. The vaccinated rabbits were vaccinated either once or twice. The amount of virus in each dose is about $1 \times 10^2$ to about $1 \times 10^8$ PFU/ml; preferably about $1 \times 10^7$ PFU/ml. After vaccination, all the vaccinated rabbits and controls were challenged orally with at least $1 \times 10^2$ PFU, preferably about $3 \times 10^5$ PFU, of virulent Ala rotavirus.

For oral challenge, 1 ml of undiluted virus or virus diluted in PBS was administered from a syringe peros using a blunt-ended feeding needle as described in Conner et al. (1988).

For single vaccine dosed rabbits, challenge with virulent Ala rotavirus may be administered about at least 14 days post-vaccination (dpv), preferably about at least 21 dpv. For twice vaccine dosed rabbits, the initial dose was administered at 0 dpv, the second dose may be administered at least 14 dpv (preferably at least 21 dpv), and the oral challenge may be administered from at least 7 days (preferably about 21 days) after the second dose. Based on the rabbit model, those skilled in the art will realize that vaccination of human infants may be done in accordance with routine immunization schedules.

Intestinal lavage and serum samples were collected from all rabbits at the timepoints outlined below in the specific examples and as previously described in Conner et al. (1991). Because of the time requirements for performing the ravage procedure, a maximum of ten rabbits could be sampled on one day. Therefore, the lavage and corresponding serum samples were collected over two days (consecutive days whenever possible) for each timepoint. For data analysis, no distinction was made between the two sampling days. Fecal samples were collected 0 to 10 days post-challenge (dpc).

Antigen ELISAs were performed using a modification of the procedure described previously in Conner et al. (1988) to measure rotavirus excretion. Briefly, the modifications were as follows: Polyvinylchloride plates were coated with 100 µl of hyperimmune guinea pig anti-Ala serum overnight at room temperature, and the wells were blocked with 200 µl of 5% skim milk in PBS for 2 hours at 37° C. The reagent volume for each subsequent step was 100 µl. The conjugate was diluted in 0.5% skim milk in PBS. A sample was considered positive if the $A_{414}$ value of the mean duplicate wells was greater than 0.1 and this absorbance value was greater than or equal to two standard deviations above the absorbance value of the negative diluent control. Serial dilutions of Ala stock virus also were included on each plate as a positive control.

ELISAs to measure total (IgA, IgM, IgG) anti-rotavirus antibody in serum and intestinal samples were performed as previously described in Conner et al. (1991) to measure antibody responses. The ELISAs to measure IgA concentration and anti-rotavirus IgA antibody in serum and intestinal samples were performed using a modification of the procedures previously described in Conner et al., (1991). Specifically, the assays were modified by use of (i) a monoclonal antibody specific for rabbit IgA (Cole, *Monoclonal Antibody News* 7:23–24 (1989)) (supplied by Carol Cole of Naval Research, Bethesda, Md.) conjugated to biotin (Guesdon et al., *J. Histo. Cyto.* 27:1131–1139 (1979)), (ii) an avidin-horseradish peroxidase (HRP) conjugate (Vector Laboratories, Inc., Burlingame, Calif.), and (iii) a TMB (3,3',5,5'-tetramethylbenzidine) substrate (Kirkegaard & Perry Laboratories, Inc., Gaithersburg, Md.). Total IgA concentrations were determined for pre- and post-challenge intestinal lavage samples. Because the IgA concentration in sequential samples for individual rabbits only varied from 1- to 4.4-fold, IgA anti-rotavirus titers were not normalized, as described previously (Conner et al. 1991)).

ELISAs to measure Ikg anti-rotavirus antibody in intestinal samples were performed identically to the total antibody ELISA (Conner et al. (1991)), except. HRP-conjugated goat anti-rabbit IgG (Hyclone Laboratories, Inc., Logan, Utah) was used as the conjugate.

All antibody titers were compared using the Wilcoxon rank sum two-sample test for unpaired samples. Because of the small number of rabbits in each vaccine group, statistical comparisons for antibody titers and days of virus excretion were made only between live and inactivated virus (in either aluminum phosphate or Freund's adjuvant) or between virus (live and inactivated)-Freund's adjuvant and virus (live and inactivated)-aluminum phosphate. The comparison of the means of days of virus excretion was performed using the Student's t test. Protection from live Ala challenge was analyzed using the Fishers exact test, two-tailed.

In the instant experiments, rabbits were protected from challenge with Ala virus after two, but not one, vaccinations with live or inactivated SA11 virus in either Freund's adjuvant or aluminum phosphate. Protection in these experiments was evaluated by examining virus shedding after challenge. None of the rabbits vaccinated twice excreted detectable virus, as detected by ELISA, whereas all control rabbits excreted virus (mean duration of shedding, 5 days). Protection from virus infection (virus excretion) following parenteral vaccination of rabbits was associated with the presence of anti-rotavirus IgG in the intestine but not anti-rotavirus IgA, as IgA was not detected in the intestine of virus-vaccinated rabbits until after the oral challenge. These results suggest that intestinal anti-rotavirus IgG antibody may mediate protection. The prior art antibody studies identified in the background of the invention support a hypothesis that protection of the rabbits was mediated by the anti-rotavirus IgG. However, the prior art studies differ significantly from the instant results in that the IgG in instant experiments was induced by active immunity stimulated by parenteral inoculation and not by passive lactogenic immunity or oral administration of IgG.

Very slight differences in reactivity to monoclonal antibodies to rotavirus surface antigens VP7 or VP4 or polyclonal antibodies to whole virus were observed by ELISA when the inactivated and live rotavirus preparations were compared prior to mixing with the adjuvants. Immune responses and protection also were compared using the two adjuvants, Freund's adjuvant and aluminum phosphate. Although the serum and intestinal antibody titers induced by live and inactivated vaccines in the two adjuvants did not appear to vary, it was not possible to statistically compare the antibody titers due to the small number of rabbits in each group. Titers induced by the two adjuvants, however, were compared by grouping the rabbits by type of adjuvant. Following two vaccinations, significantly higher serum anti-rotavirus titers were induced in rabbits vaccinated with Freund's adjuvant as compared to rabbits vaccinated with aluminum phosphate adjuvant, although protection was observed in both groups. However, these two adjuvants did not induce significant differences in IgG or total anti-rotavirus titers in the intestine, which would account for the equivalent levels of protection induced by both vaccine-adjuvant formulations.

A statistically significant difference in serum titers induced by the two adjuvants remained following challenge. This was not surprising, since little or no increase in serum titer was observed following challenge. Since these rabbits were protected from detectable virus infection, it is likely that no or minimal viral replication occurred in the intestine. The input dose of challenge virus or the limited virus replication might be sufficient to induce or boost an intestinal but not a serologic response. Intestinal antibody induction (IgA) was observed in all but one of the rabbits and boosting of IgG and total Ig was observed in three of the rabbits.

All but one of the virus-vaccinated rabbits had detectable IgA responses following oral challenge with live virus. These results indicate that a combined parenteral-oral or oral-parenteral vaccination regimen also could be used to induce intestinal IgG and IgA immunity.

The present invention is not restricted to the use of simian rotavirus SA11 clone 3 which is herein described and used for exemplification purposes only. The invention applies to the use of any cultivatable serotype 3 rotavirus or any other cultivatable serotype where a human rotavirus is represented. Serotype, as it is used herein, means a classification of viruses by a specific neutralizing antibody/antigen reaction.

EXAMPLE 1

Preparation of Rotavirus Vaccine

Virus. Both the simian rotavirus SA11 clone 3, used as the vaccine, and the Ala rabbit rotavirus, used for rabbit challenge inoculations and for enzyme-linked immunoabsorbent assay (ELISA), have been described previously by Conner et al. (1988); Tanaka et al., *Arch. Virol.* 98:253–265 (1988); Thouless et al, *Arch. Virol.* 89:161–170 (1986); and Ericson et al., *J. Virol.* 43:825–839 (1982). Both simian rotavirus SA11and Ala rabbit rotavirus are serotype 3, based on their VP7 reactivity. Tanaka, et al., (1988); Thouless et al. (1986); Hoshino et al., *J. Infect. Dis.* 149:694–702 (1984). These viruses were cultivated in fetal rhesus monkey kidney (MA 104) cells in the presence of trypsin, as previously described in Conner et al., (1988).

Virus Inactivation. The vaccine preparations were made with SA11-infected MA104 cell lysates. The lysates were made by harvesting infected MA104 cells; at maximum cytopathic effect and freezing, thawing, and sonicating the cells. Inactivated virus was prepared by treatment with formalin (diluted serially in tissue culture media M199 to about 0.00925% final concentration) at about 37° C. on a shaker using the following procedure: Samples of virus were collected at 0, 10, 20, 30, and 60 minutes and at 2, 4, 6, 24, 48 and 72 hours after the addition of formalin for testing the level of virus inactivation by plaque assay. Residual formalin was neutralized by the addition of sodium bisulfite (150 ll/ml of virus of a 0.35% solution) to each sample taken at each timepoint and to the whole virus preparation at 72 hours.

A control SA11 sample was not treated with formalin but was incubated at about 37° C. on a shaker for about 72 hours and then stored at 4° C. The inactivated and control SA11 virus preparations were stored at 4° C. until titration, adsorption to aluminum phosphate, or mixed with Freund's adjuvant. The virus preparation inactivated with formalin for 72 hours was used as the vaccine.

Inactivation of SA11 proceeded rapidly with a decrease in titer from $10^7$ PFU to $10^{4.5}$ PFU during an initial 6-hour period (FIG. 1). The slope of the inactivation curve decreased following this initial period, and complete inactivation occurred by 48 hours.

Preparation of the virus vaccines. The SA11 virus was adsorbed to aluminum phosphate using the following procedure: Live and inactivated SA11 virus preparations were diluted in phosphate-buffered saline (PBS) to yield about $2\times10^7$ plaque forming units (PFU) of virus (based on the original titer of the preparation), sonicated and clarified at 1500 rpm fur 15 minutes. The aluminum phosphate was mixed on a shaker at 4° C. for several hours prior to the addition of about 0.07 ml of aluminum phosphate per 1 ml of virus. The aluminum phosphate was added at a rate of 0.5 ml per 5 to 10 minutes until all the aluminum phosphate had been added, and the virus-aluminum phosphate mixture then was shaken an additional 2 hours. The aluminum phosphate-adsorbed virus preparations then were centrifuged at 10,000×g for 10 minutes. The supernatant was removed and kept, and the pellet was suspended in PBS to the original volume and stored at 40° C. until used.

A control preparation of PBS was treated in an identical manner. The efficiency of adsorption was determined by immunoblots, by comparing the endpoint titers of the supernatant, pellet, and untreated material. It was estimated that the efficiency of adsorption was approximately 50%.

The SA11 vaccine preparation in Freund's adjuvant was prepared as follows to ensure that the SA11-Freund's adjuvant vaccine dose contained the same amount of SA11 antigen as the aluminum phosphate-virus preparations. It was estimated that the amount of virus in 1 ml of the aluminum phosphate-SA11 preparation was $1\times10^7$ PFU, because the efficiency of adsorption of virus to aluminum phosphate was found to be to 50% of the original preparation ($2\times10^7$ PFU) prior to adsorption. Therefore, for the live and inactivated SA11-Freund's vaccines, the virus was diluted to yield $1\times10^7$ PFU/ml, after being mixed (1:1) with complete Freund's adjuvant (first vaccine dose) or incomplete Freund's adjuvant (second vaccine dose). A control PBS-Freund's preparation was prepared in the same manner.

The live virus-aluminum phosphate, inactivated virus-aluminum phosphate, inactivated virus-Freund's and live virus-Freund's formulations described above are referred to herein as virus-adjuvant formulations. The PBS-aluminum phosphate and PBS-Freund's formulations described above are referred to herein as PBS-adjuvant formulations or PBS controls.

EXAMPLE 2

Single Dose Potency of Rotavirus Vaccine

Rabbits, inoculations and sample collections. Rabbits, 5 to 6 months old from 5 different litters, used in this study were from a specific-pathogen (rotavirus) free colony reared in isolator units, as previously reported (Conner et al. (1989, 1991)). For the experiments, rabbits were removed from the colony and housed in either isolator or open cages in a BL2 containment facility at Baylor College of Medicine. All rabbits, except four control animals (see below), were vaccinated intramuscularly with 1ml of a virus-adjuvant or PBS-adjuvant formulation described in Example 1. The virus-adjuvants used were live virus-aluminum phosphate, inactivated virus-aluminum phosphate, inactivated virus-Freund's and live virus-Freund's. The virus used was serotype 3 rotavirus, SA11. However, any serotype 3 rotavirus or any other cultivatable serotype where a human rotavirus is represented may be used. The inactivated virus, virus-adjuvant formulations and PBS controls were prepared as described in Example 1. The same lot of virus or vaccine preparation was used to vaccinate all rabbits. All rabbits were challenged orally with $3\times10^5$ PFU of Ala virus. Intestinal lavage and serum samples were collected from all rabbits at the timepoints outlined below and in Table 1.

Sixteen rabbits were vaccinated once at 0 dpv and challenged at 20 dpv. Serum and intestinal lavage samples were collected prior to vaccination, 17 to 18 dpv, and 41 to 45 dpv (20 to 24 dpc). One rabbit from each of two vaccination groups (live virus-Freund's and live virus-aluminum phosphate) died of an unrelated (non-rotavirus) diarrheal disease (necrotizing enterocolitis) prior to challenge. These rabbits were excluded from analysis.

Immune response and protection following one vaccine dose. All rabbits were rotavirus antibody negative prior to the start of these experiments and all control rabbits remained antibody negative until after challenge (Table 1). All vaccinated rabbits seroconverted by 17 to 18 dpv and no statistically significant differences in titers were observed between live and inactivated virus in either adjuvant, or between virus in aluminum phosphate or in Freund's adjuvant. Only two rabbits had detectable intestinal total antibody responses (titer=5) at 17 to 18 dpv.

No protection from challenge (20 dpv), as determined by virus excretion, and no statistically significant difference was observed in the mean number of days of virus excretion between rabbits vaccinated with live SA11-adjuvant (mean 5.75 days) or inactivated SA11-adjuvant (mean 5.16 days), or between SA11-aluminum phosphate (mean 4.6 days) and SA11-Freund's adjuvant (mean 6.2 days) or control groups (mean 5.75 days). No statistically significant differences in serologic antibody responses were observed between any of the virus vaccinated groups after challenge, although all rabbits had 4-fold or greater increases in titers after challenge. All rabbits had detectable intestinal total antibody responses following challenge. An unexpected finding was that following challenge, intestinal IgG-specific anti-rotavirus antibody was detected in all the virus-vaccinated rabbits and one control animal. All but one rabbit developed an IgA anti-rotavirus response following challenge.

EXAMPLE 3

Serial Dose Potency of Rotavirus Vaccine

Rabbits, inoculations and sample collections. Rabbits, as described in Example 2, were from a specific-pathogen (rotavirus) free colony reared in isolator units. All rabbits, except four control animals (see below), were twice vaccinated intramuscularly with 1 ml of the virus-adjuvant or PBS-adjuvant formulations described in Example 1 about 49 days apart. The virus-adjuvants used were live virus-aluminum phosphate, inactivated virus-aluminum phosphate, inactivated virus-Freund's and live virus-Freund's. The virus used was serotype 3 rotavirus, SA11. However, any serotype 3 rotavirus or any other cultivatable serotype where a human rotavirus is represented may be used. The inactivated virus, virus-adjuvant formulations and PBS controls were prepared as described in Example 1. The same lot of virus or vaccine preparation was used to vaccinate all rabbits. All rabbits were challenged orally with $3\times10^5$ PFU of Ala virus. Intestinal lavage and serum samples were collected from all rabbits at the timepoints outlined below and in Table 2.

Eighteen rabbits were vaccinated on day 0, boosted at 49 dpv and challenged at 71 dpv (22 days after the second vaccination). One rabbit from each of four vaccination groups [live virus-aluminum phosphate, inactivated virus-aluminum phosphate, inactivated virus-Freund's and PBS-Freund's]died of an unrelated diarrheal illness (see above) that occurred during the course of the experiment. These rabbits were excluded from analysis. At 83 dpv four additional non-vaccinated control animals were added to the experiment. Serum or intestinal lavage samples or both were collected prior to vaccination, 49 dpv (serum sample only), 83 to 84 dpv (14 to 15 days after the second vaccination), and 91 to 92 dpv (20 to 21 dpc).

Immune response and protection following two vaccine doses. All rabbits were rotavirus antibody negative prior to the start of the experiment and all control rabbits remained antibody negative until after challenge (Table 2). All vaccinated rabbits seroconverted after the first vaccine dose, and the serum antibody titers elicited by the SA11-Freund's adjuvant vaccines (live and inactivated grouped together) were higher than the titers elicited by the SA11-aluminum phosphate vaccines ($P<0.02$). Following the second vaccine dose, the antibody titers of the SA11-aluminum phosphate vaccinated rabbits increased significantly ($P<0.05$), although they were still lower in titer than those elicited by SA11-Freund's adjuvant ($P<0.05$). Based on the lack of response after one vaccine dose in the previous experiment, intestinal lavage samples were not collected after the first vaccine dose in this experiment. Fourteen to fifteen days after the second vaccine dose was administered (63 to 64 dpv) all rabbits had detectable total (IgA, IgM, IgG) antibody in the intestine (Table 2). No intestinal IgA anti-rotavirus antibody was detected; however, intestinal IgG anti-rotavirus antibody was detected in all the vaccinated rabbits (titer range, 10 to 320). No statistically significant differences in IgG or total Ig titers in the intestine were observed between rabbits vaccinated with live virus or inactivated virus in either adjuvant or with virus in either Freund's adjuvant or aluminum phosphate.

Following challenge at 71 dpv, all five control rabbits excreted virus for 4 to 6 days (mean 5 days) (Table 2). None of the SA11-vaccinated rabbits excreted virus, indicating that they were actively protected from live virulent Ala virus challenge by parenteral vaccination with SA11 virus. The difference in the number of vaccinated and control rabbits that shed virus was statistically significant ($P=0.001$).

All 5 control rabbits seroconverted following Ala virus challenge. Serum anti-rotavirus titers of the virus vaccinated rabbits changed very little following challenge; only one rabbit (No. 9) had a significant change (4-fold decrease) in titer. The final serum titers elicited by oral challenge in the control rabbits were lower than those elicited by parenteral SA11-Freund's vaccine ($P<0.02$), but they were higher than those elicited by parenteral SA11-aluminum phosphate vaccine ($P<0.05$).

Following challenge, intestinal antibody conversion occurred in all five, control rabbits. High titers of anti-rotavirus IgA antibody were elicited in the control rabbits following oral challenge. Intestinal IgA anti-rotavirus antibody also was elicited in all but one vaccinated rabbit (No. 7), indicating that the IgG that was present at the time of the oral challenge did not interfere with the induction of a local IgA response. In 3 of 9 vaccinated rabbits, 4-fold or greater increases in intestinal IgG anti-rotavirus antibody titers were observed, whereas in one rabbit (No. 7) a 16-fold decrease in intestinal IgG titer was observed. Two of five control rabbits also had high titers of intestinal IgG anti-rotavirus antibody after challenge.

EXAMPLE 4

Combined Oral Parenteral Vaccination

Rabbits, as described in Example 2, are from a specific-pathogen (rotavirus) free colony. Rabbits are vaccinated intramuscularly at least once with about 1 ml of the virus-adjuvant described in Example 1 on 0 dpv. Preferably, a second intramuscular vaccination occurs at least 14 dpv, most preferably at least 21 dpv. The virus-adjuvant used is selected from live virus-aluminum phosphate, inactivated virus-aluminum phosphate, inactivated virus-Freund's and live virus-Freund's. The virus is SA11, any serotype 3 rotavirus, or any other cultivatable serotype where a human rotavirus is represented. The inactivated virus, virus-adjuvant formulations and PBS controls are prepared as described in Example 1. Rabbits then are vaccinated orally with at least $1\times10^2$ PFU, preferably $3\times10^5$ PFU, of live or inactivated SA11, live or inactivated Ala virus, or any rotavirus vaccine known in the art. The oral vaccine may be administered at least 7 days, preferably at least 21 days, after the last intramuscular injection.

EXAMPLE 5

Combined Oral Parental Vaccination

Rabbits, as described in Example 2, are from a specific-pathogen (rotavirus) free colony. Rabbits are vaccinated orally at least once with at least $1\times10^2$ PFU, preferably $3\times10^5$ PFU, of live or inactivated SA11, live or inactivated Ala virus, or any rotavirus vaccine known in the art. Rabbits then are vaccinated intramuscularly at least once with 1 ml of the virus-adjuvant described in Example 1 at least 7 days, preferably at least 21 days, after the oral vaccine. The virus-adjuvant used is selected from live virus-aluminum phosphate, inactivated virus-aluminum phosphate, inactivated virus-Freund's and live virus-Freund's. The virus is SA11, a serotype 3 rotavirus, or any other cultivatable serotype where a human rotavirus is represented. The inactivated virus, virus-adjuvant formulations and PBS controls are prepared as described in Example 1.

EXAMPLE 6

Combined Parenteral and Subunit Vaccination

Rabbits, as described in Example 2, are from a specific-pathogen (rotavirus) free colony. Rabbits are twice vaccinated intramuscularly on 0 dpv and on at least 14–49 dpv. Preferably the second vaccination occurs at least 21 dpv. A virus-adjuvant is used for one of the two vaccinations. A rotavirus subunit vaccine-adjuvant is used for the other.

The virus-adjuvant is selected from live virus-aluminum phosphate, inactivated virus-aluminum phosphate, inactivated virus-Freund's and live virus-Freund's described in Example 1. The virus is a serotype 3 rotavirus or any other cultivatable serotype where a human rotavirus is represented. The inactivated virus, virus-adjuvant formulations and PBS controls are prepared. 1 ml of the virus-adjuvant described in Example 1 is administered during vaccination.

The rotavirus subunit vaccine used may be any vaccine produced from a combination of two or more rotavirus proteins selected from the group consisting of VP1, VP2, VP3, VP4, VP6, VP7, VP9 NS35, NS34 and NS28. Preferably, the subunit vaccine is made from recombinant molecules. Any method of producing the recombinant molecules is acceptable. The following method of producing the recombinant molecules, however, is preferred: (a) inserting at least two rotavirus genes selected from the group of rotavirus genes consisting of gene 1, gene 2, gene 3, gene 4, gene 5, gene 6, gene 7, gene 8, gene 9, gene 10, gene 11, into a baculovirus transfer vector; (b) transferring said at least two rotavirus genes in the baculovirus transfer vector to the baculovirus *Autographa californica* nuclear polyhedrosis virus genome DNA by cotransfection of *Spodoptera frugiperda* with wild type *Autographa callifornica* nuclear polyhedrosis virus DNA; (c) selecting the recombinant polyhedrin promoter- rotavirus gene molecule by identifying occlusion-negative plaques or by hybridization with specific gene probes or by both procedures; and (d) purifying said plaques to obtain virus stocks containing the recombinant molecule. Most preferably, the: subunit vaccine is produced from a combination of two or more of VP2, VP4, VP6 and VP7. The subunit vaccine may be administered with an adjuvant, for example Freund's adjuvant or aluminum phosphate. 1 ml of the subunit vaccine is administered at a rate of at least 0.5 $\mu$g, preferably about 20 $\mu$g, rotavirus protein per ml of vaccine-adjuvant.

EXAMPLE 7

Passive Immunity

Passive immunization of human or animal infants against rotavirus infection may be achieved by actively immunizing a mother as described above in Examples 2 through 6 under one of three immunization scenarios: a) immunize the mother with an initial dose and a booster before her infant is born, b) immunize the mother with an initial dose before her infant's birth and a booster while the mother is nursing, or c) immunize the mother with an initial dose and a booster while the mother is nursing the infant.

TABLE 1

Serum and intestinal ELISA antibody responses to one vaccination with SA11 and challenge with Ala virus

| | | | Total serum anti-rotavirus antibody titer at indicated DPV[a] (DPC)[b] | | | Intestinal isotype-specific anti-rotavirus antibody titer at indicated DPV (DPC) | | | | | | |
|---|---|---|---|---|---|---|---|---|---|---|---|---|
| | | | | | 41–45 | Pre | 17–18 | 41–45 (20–24) | | | DPC | Protection |
| Rabbit | Virus | Adjuvant | Pre | 17–18 | (20–24) | Total | Total | IgA | IgG | Total | virus shed | from challenge |
| 1 | Inac | Freund's | <50 | 12,800 | >409,600 | <5 | <5 | 160 | 3,200 | 640 | 2–8 | No |
| 2 | Inac | Freund's | <50 | 6,400 | 409,600 | <5 | <5 | <5 | 3,200 | 1,600 | 1–6 | No |
| 3 | Inac | Freund's | <50 | 25,600 | 409,600 | <5 | <5 | 20 | 80 | 800 | 2–6 | No |
| 4 | Live | Freund's | <50 | 3,200 | 102,400 | <5 | 5 | 80 | 320 | 160 | 2–8 | No |
| 5 | Live | Freund's | <50 | 3,200 | 204,800 | <5 | <5 | 640 | 20 | 160 | 3–8 | No |
| 6 | PBS | Freund's | <50 | <100 | 51,200 | <5 | <5 | 160 | <5 | 80 | 2–7 | No |
| 7 | PBS | Freund's | <50 | <100 | 25,600 | <5 | <5 | 80 | <5 | 20 | 4–8 | No |
| 8 | Inac | Alum | <50 | 1,600 | 102,400 | <5 | <5 | 40 | 10 | 80 | 5–7 | No |
| 9 | Inac | Alum | <50 | 3,200 | 102,400 | <5 | '5 | 20 | 40 | 80 | 3–6 | No |
| 10 | Inac | Alum | <50 | 1,600 | 204,800 | <5 | <5 | ND[c] | 3,200 | 3,200 | 2–7 | No |
| 11 | Live | Alum | <50 | 6,400 | 409,600 | <5 | <5 | 80 | 80 | 320 | 2–7 | No |
| 12 | Live | Alum | <50 | 12,800 | 204,800 | <5 | 5 | 320 | 3,200 | 3,200 | 3–6 | No |
| 13 | PBS | Alum | <50 | <100 | 25,600 | <5 | <5 | ND | 640 | 160 | 3–8 | No |
| 14 | PBS | Alum | <50 | <100 | 12,800 | <5 | <5 | ND | <5 | 80 | 3–8 | No |

[a]DPV, days post-vaccination. Vaccine administered at 0 DPV.
[b]DPC, days post-challenge. Rabbits were challenged with $3 \times 10^5$ PFU of Ala virus at 21 DPV.
[c]ND, not done.

TABLE 2

Comparison of the active serum and intestinal immune response and protection from challenge with Ala rotavirus following two parenteral vaccinations with SA11 virus

| | | | Total serum and anti-rotavirus antibody titer at indicated DPV[a] (DPC)[b] | | | | Intestinal isotype-specific anti-rotavirus antibody titer at indicated DPV (DPC) | | | | | | | | |
|---|---|---|---|---|---|---|---|---|---|---|---|---|---|---|---|
| | | | | | | | Pre | | | | | | | DPC | Protection |
| | | | | | | 91–92[d,f] | IgA & | 63–64 | | | 91–92 (20–21) | | | virus | from |
| Rabbit | Virus | Adjuvant | Pre | 49[c] | 63–64[d,e] | (20–21) | Total | IgA | IgG | Total | IgA | IgG | Total | shed[g] | challenge |
| 1 | Inac | Freund's | <50 | 51,200 | 102,400 | 102,400 | <5 | <5 | 80 | 40 | 80 | 1,280 | 320 | None | Yes |
| 2 | Inac | Freund's | <50 | 25,600 | 51,200 | 102,400 | <5 | <5 | 10 | 10 | 40 | 320 | 160 | None | Yes |

TABLE 2-continued Comparison of the active serum and intestinal immune response and protection from challenge with Ala rotavirus following two parenteral vaccinations with SA11 virus

| | | | Total serum and anti-rotavirus antibody titer at indicated DPV[a] (DPC)[b] | | | | Intestinal isotype-specific anti-rotavirus antibody titer at indicated DPV (DPC) | | | | | | | | |
|---|---|---|---|---|---|---|---|---|---|---|---|---|---|---|---|
| | | | | | | | Pre | | | | | | | DPC | Protection |
| | | | | | | 91–92[d,f] | IgA & | 63–64 | | | 91–92 (20–21) | | | virus | from |
| Rabbit | Virus | Adjuvant | Pre | 49[c] | 63–64[d,e] | (20–21) | Total | IgA | IgG | Total | IgA | IgG | Total | shed[g] | challenge |
| 3 | Live | Freund's | <50 | 102,400 | 102,400 | 204,800 | <5 | <5 | 20 | 20 | 5 | 20 | 40 | None | Yes |
| 4 | Live | Freund's | <50 | 819,200 | 204,800 | 204,800 | <5 | <5 | 320 | 160 | 20 | 160 | 320 | None | Yes |
| 5 | Live | Freund's | <50 | 409,600 | 102,400 | 102,400 | <5 | <5 | 320 | 160 | 10 | 160 | 40 | None | Yes |
| 6 | Inac | Alum | <50 | 800 | 12,800 | 25,600 | <5 | <5 | 20 | 20 | 160 | 10,240 | 5,120 | None | Yes |
| 7 | Inac | Alum | <50 | 1,600 | 12,800 | 6,400 | <5 | <5 | 160 | 80 | <5 | 10 | 10 | None | Yes |
| 8 | Live | Alum | <50 | 3,200 | 25,600 | 12,800 | <5 | <5 | 20 | 20 | 10 | 10 | 20 | None | Yes |
| 9 | Live | Alum | <50 | 3,200 | 25,600 | 6,400 | <5 | <5 | 40 | 20 | 10 | 20 | 20 | None | Yes |
| 10 | PBS | Alum | <50 | <50 | <50 | 51,200 | <5 | <5 | <5 | <5 | 320 | <5 | 320 | 5–9 | No |
| 11 | None | None | NA[h] | NA | <50 | 25,600 | NA | <5 | <10 | <5 | 160 | <5 | 160 | 4–7 | No |
| 12 | None | None | NA | NA | <50 | 51,200 | NA | <5 | <10 | <5 | 160 | <5 | 40 | 5–9 | No |
| 13 | None | None | NA | NA | <50 | 51,200 | NA | <5 | <10 | <5 | 320 | 640 | 640 | 3–8 | No |
| 14 | None | None | NA | NA | <50 | 51,200 | NA | <5 | <10 | <5 | 160 | 320 | 160 | 2–6 | No |

[a]DPV, days post-vaccination. Vaccine was administered on 0 DPV and the rabbits were boosted on 49 DPV.
[b]DPC, days post-challenge. Rabbits were challenged with $3 \times 10^5$ PFU of Ala virus at 71 DPV (22 days after second vaccine).
[c]Significantly highter antibody titers obtained with SA11-Freund's adjuvant than with SA11-alum ($P < 0.02$).
[d]Significantly higher antibody titers obtained with SA11-Freund's adjuvant than with SA11-alum ($P < 0.05$).
[e]Significant increase in antibody titers obtained after second vaccine dose of SA11-alum ($P < 0.05$).
[f]Significantly higher antibody titers obtained after oral challenge of controls than with SA11-alum ($P < 0.05$).
[g]Significant difference in number of vaccinated and control rabbits that shed virus ($P = 0.001$).
[h]NA, not applicable.

What is claimed is:

1. A method for actively immunizing animals or humans against rotavirus infection, comprising:
    parenterally administering a first immunogenic composition comprising about $1 \times 10^2$ to about $1 \times 10^8$ PFU/ml of a live virus classified in a rotavirus serotype which included at least one human rotavirus, and
    parenterally administering a subsequent immunogenic composition, said subsequent immunogenic composition comprising about $1 \times 10^2$ to about $1 \times 10^8$ PFU/ml of a live virus classified in a rotavirus serotype which includes at least one human rotavirus.

2. The method of claim 1 wherein said first immunogenic composition and said subsequent immunogenic composition each comprise about $1 \times 10^7$ PFU/ml of virus.

3. The method of claim 1 wherein said subsequent immunogenic composition is administered at least 14 days after the administration of said first immunogenic composition.

4. A method for immunizing animals or humans against rotavirus infection, comprising the steps of:
    (a) parentally administering an immunogenic composition comprising about $1 \times 10^2$ to about $1 \times 10^8$ PFU/ml of a live virus classified in a rotavirus serotype which includes at least one human rotavirus; and
    (b) parenterally administering immunogenic composition comprising about $1 \times 10^2$ to about $1 \times 10^8$ PFU/ml of an inactivated form of any virus classified in said rotavirus genotype which includes at least one human rotavirus,
    wherein steps (a) and (b) may be performed in any order.

5. The method of claim 4, wherein said rotavirus serotype which includes at least 1 one human rotavirus selected from the troup consisting of serotpe 1, serotype 2, serotype 3, serotype 4, serotype 8, serotype 9, serotype 10 and serotype 12.

6. The method of claim 4, wherein said immunogenic composition comprising a live virus contains about $1 \times 10^7$ PFU/ml of virus and said immunogenic composition comprising an inactivated virus contains about $1 \times 10^7$ PFU/ml of virus.

7. The method of claim 4, wherein steps (a) and (b) are performed at least 14 days apart.

8. A method for passively immunizing animal or human infants against rotavirus infection comprising the steps of:
    (a) parenterally administering to a mother before her infant's birth immunogenic composition comprising about $1 \times 10^2$ to about $1 \times 10^8$ PFU/ml of a live virus classed in a rotavirus serotype which includes at least one human rotavirus; and
    (b) parenterally administering to said mother before her infant's birth a immunogenic composition comprising about $1 \times 10^2$ to about $1 \times 10^8$ PFU/ml of an inactivated form of any virus classified in said rotavirus serotype which includes at least one human rotavirus,
    wherein steps (a) and (b) may be performed in any order and are performed at least 14 days part.

9. A method for passively immunizing animal or human infants against rotavirus infection comprising the steps of:
    (a) parenterally administering to a nursing mother an immunogenic composition comprising about $1 \times 10^2$ to about $1 \times 10^8$ PFU/ml of a live virus classified in a rotavirus which includes at least one human rotavirus; and
    (b) parenterally administering to said nursing mother an immunogenic composition comprising about $1 \times 10^2$ to about $1 \times 10^8$ PFU/ml of an inactivated form of any virus classified in said rotavirus serotype which includes at least one human rotavirus,
    wherein steps (a) and (b) may be performed in any order.

10. A method for passively immunizing animal or human infants against rotavirus infection, comprising the steps of:
    (a) parenterally administering to a nursing mother an immunogenic composition comprising about $1 \times 10^2$ to about $1\times10^8$ PFU/ml of a live or inactivated virus classified in a rotavirus serotype which includes at least one human rotavirus; and (b) orally administering at least $1\times10^2$ PFU of a rotavirus an immunogenic composition to said mother, wherein said steps (a) and (b) may be performed in any order.

11. A method for passively immunizing animal or human infants against rotavirus infection, comprising the steps of:

(a) parenterally administering to a mother an immunogenic composition comprising about $1\times10^2$ to about $1\times10^8$ PFU/ml of a live or inactivated virus classified in a rotavirus serotype which includes at least one human rotavirus;

(b) parenterally administering to a mother an immunogenic composition comprising at least 0.5 $\mu$g of a rotavirus subunit; and wherein said steps (a) and (b) may be performed in any order.

12. A method for passively immunizing animal or human infants against rotavirus infection, comprising the steps of:

(a) parenterally administering to a mother immunogenic composition comprising about $1\times10^2$ to about $1\times10^8$ PFU/ml of a live virus classified in a rotavirus serotype which includes at least one human rotavirus; and (b) parenterally administering to a mother an immunogenic composition comprising about $1\times10^2$ to about $1\times10^8$ PFU/ml of an inactivated form of any virus classified in a rotavirus serotype which includes at least one human rotavirus, wherein said steps (a) and (b) may be performed in any order, and wherein one of said steps is carried out before the birth of said mother's infant and the other of said steps is carried out while said mother is nursing said infant.

13. A method for passively immunizing animal or human infants against rotavirus infection, comprising the steps of:

(a) parenterally administering to a mother immunogenic composition comprising about $1\times10^2$ to about $1\times10^8$ PFU/ml of a live or inactivated virus classified in a rotavirus serotype which includes at least one human rotavirus; and (b) orally administering at least $1\times10^2$ PFU of a rotavirus an immunogenic composition to said mother, wherein said steps (a) and (b) may be performed in any order, and wherein one of said steps is carried out before the birth of said mother's infant and the other of said steps is carried out while said mother is nursing said infant.

14. A method for passively immunizing animal or human infants against rotavirus infection, comprising the steps of:

(a) parenterally administering to a mother an immunogenic composition comprising about $1\times10^2$ to about $1\times10^8$ PFU/ml a live or inactivated virus classified in a rotavirus serotype which includes at least one human rotavirus;

(b) parenterally administering to a mother immunogenic composition comprising at least 0.5 $\mu$g of a rotavirus subunit; and wherein said steps (a) and (b) may be performed in any order, and wherein one of said steps is carried out before the birth of said mother's infant and the other of said steps carried out while said mother is nursing said infant.

* * * * *